United States Patent
Tu et al.

[11] Patent Number: 5,891,027
[45] Date of Patent: *Apr. 6, 1999

[54] CARDIOVASCULAR CATHETER SYSTEM WITH AN INFLATABLE SOFT TIP

[75] Inventors: Hosheng Tu, Tustin; Chi-Wu James Chang, Cerritos, both of Calif.

[73] Assignee: Irvine Biomedical, Inc., Irvine, Calif.

[*] Notice: This patent issued on a continued prosecution application filed under 37 CFR 1.53(d), and is subject to the twenty year patent term provisions of 35 U.S.C. 154(a)(2).

[21] Appl. No.: 735,199

[22] Filed: Oct. 21, 1996

[51] Int. Cl.⁶ ........................................... A61B 5/04
[52] U.S. Cl. ..................... 600/374; 607/122; 606/41; 604/96
[58] Field of Search ........................... 128/642; 607/122; 600/116, 139, 140, 143, 152, 206, 373, 374, 377, 381; 604/95, 96, 266, 264, 280, 282; 606/192, 41

[56] References Cited

U.S. PATENT DOCUMENTS 5,345,936  9/1994  Pomeranz et al. ...................... 128/642
5,555,883  9/1996  Avitall ..................................... 128/642

*Primary Examiner*—Kenneth E. Peterson
*Assistant Examiner*—David M. Ruddy

[57] ABSTRACT

A cardiovascular catheter system or catheter probe system suitable for electrophysiology mapping and radiofrequency ablation of cardiac tissue comprises a catheter shaft having a proximal end, a distal handle, and a lumen extending therebetween, whereby a distal portion of the shaft is deflectable; and the soft distal section is inflatable to conform intimately to the irregular intracardiac tissue surface.

6 Claims, 4 Drawing Sheets

CARDIOVASCULAR CATHETER SYSTEM WITH AN INFLATABLE SOFT TIP

FIELD OF THE INVENTION

The present invention generally relates to improved constructions for cardiovascular catheters. More particularly, this invention relates to methods and apparatus for diagnosing and treating cardiac arrhythmias via a cardiovascular catheter system having one or more of the catheter shafts with a pre-shaped soft tip section which may be inflated.

BACKGROUND OF THE INVENTION

Symptoms of abnormal heart rhythms are generally referred to as cardiac arrhythmias, with an abnormally rapid rhythm being referred to as tachycardia. The present invention is concerned with the treatment of tachycardias which are frequently caused by the presence of an "arrhythmogenic region" or "accessory atrioventricular pathway" close to the inner surface of the chambers of a heart. The heart includes a number of normal pathways which are responsible for the propagation of electrical signals from upper to lower chamber necessary for performing normal function. The presence of arrhythmogenic region or accessory pathways can bypass or short circuit the normal pathways, potentially resulting in very rapid heart contractions, referred to here as tachycardias.

Cardiac mapping is used to locate aberrant electrical pathways and currents emanating within the heart. The aberrant pathways cause the contractions of the heart muscle to take on abnormal and life threatening dysrhythmias. Intracardiac mapping requires careful positioning of a plurality of catheters of multiple electrodes within the heart. For example, Webster, Jr. U.S. Pat No. 4,960,134 show the general use of a catheter, Desai U.S. Pat. No. 4,940,064 show the use of generally planar mapping arrays, Chilson U.S. Pat. No. 4,699,147 shows the use of a three dimensional basket mapping array, Houser U.S. Pat. No. 5,313,943 shows the use of a fluid flow conduit, and Imran U.S. Pat. No. 5,409,000 shows the use of ultrasonic markers of a basket array. It is important for a catheter or a catheter system to intimately contact the tissue for effective and time-saving mappings with minimum fluoroscopic exposure.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying cause. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a clinician to be able to accurately steer the catheter to the region for ablation. Once at the region, it is important for a catheter to intimately contact the tissue to effectively control the emission of energy to ablate the tissue within the heart.

Regardless of the type of mapping means or ablation means used, the clinician is called upon to remotely move and manipulate the catheters in various ways. First, a catheter is inserted into a major vein or artery, usually in the neck or groin area. It is then guided into chambers of the heart by appropriate manipulation through the vein or artery. The distal tip section of a catheter must be manipulatable by a user from the proximal end of the catheter, so that the electrodes at the tip section can be positioned against the tissue region at the desired location to assure that all aberrant electrical pathways are mapped.

The development of prior mapping catheters has focused upon the requirements of in vitro mapping mechanisms. It requires the tip section including the electrodes as well as the catheter shaft to form a smooth continuous curve that may not intimately contact the non-smooth intracardiac tissue. The prior development has overlooked the important need to intimately contact the tissue by the electrodes, not the inter-electrode shaft itself, especially under the circumstances of the irregular intracardiac tissue contour. The intimate contacting of the electrodes alone of a catheter tip section via an inflatable tip shaft against the target tissue ensures effective cardiac mapping or ablation.

SUMMARY OF THE INVENTION

The present invention provides an improved cardiovascular catheter system which can be used in mapping and ablating the arrhythmogenic region. The improved catheter provides an intimate tissue contact so that reliable mapping signals can be obtained and/or desired ablation energy can be applied effectively. In one embodiment, a cardiovascular catheter of this invention comprises a catheter shaft having a distal end, a proximal end, and a lumen extending therebetween, whereby a distal portion of the shaft is deflectable; and an inflatable soft tip section. The soft tip section in this invention may include polyethylene, polyethylene terephthalate, silicone, polyurethane, or a the like material which can be formed as a thin wall tubular shaft or "balloon" and be inflated thereafter during intended clinical procedures. The thin wall tubular shaft may be either compliant such as those made of silicone and polyurethane, or non-compliant such as those made of polyethylene and polyethylene terephthalate.

The pressure to inflate the soft tip section is generally higher than the in vivo heart chamber pressure. The non-inflation pressure in this invention is defined as the pressure lower than the designated inflation pressure, such as that equal or lower than half an atmosphere pressure than the in vivo heart chamber pressure. The inflation fluid can be either saline or saline solution containing a contrast agent for fluoroscopy imaging. The inflatable soft tip section may be pre-shaped at a simulated inflation pressure to a curvature which conforms intimately to the intracardiac surface. The catheter itself possesses a relatively straight configuration under no inflation pressure. This shall render the catheter easy to be inserted into or discharged from the cardiovascular system. After the inserted catheter is in place, the soft tip section starts to curve under an inflation pressure. The tip section curvature is proportional to the inflation pressure until it reaches its pre-shape status at a pre-determined inflation pressure. This type of curving under an inflation pressure can be achieved by a double-lumen soft tip. The inflation pressure is applied to the outer lumen to force the soft tip to curve conforming to the pre-shaped pattern while the inner side lumen is kept at nominal pressure. The curved tip section under an inflation pressure is resilient and can be slightly pushed from the proximal end against the tissue so that all the electrodes contact intimately the tissues for mapping or ablation purposes.

In another embodiment, the improved catheter system has core wires extending from the proximal handle through the central lumen and being attached to the distal end of the shaft, having a steerable mechanism. In this embodiment, the ultimate tip curve shape of an inflatable soft tip section of the catheter is controlled by the steerable mechanism.

However, the intimate contact between the electrodes and the tissue is assisted via the resilient tip section under an inflation pressure.

In still another embodiment, the exterior surface of the soft tip section is consisted of a wavy pattern. The band electrodes shall be placed right on the peak of the wavy soft shaft. The electrodes are preferred to form a round surface so that the contact point of the catheter to the intracardiac tissue is through the round "hill" surface of the electrodes, instead of the bare inter-electrode shaft surface. The circumferential diameter of an electrode is generally larger than the tubing shaft diameter.

Signal conducting electrodes are placed on the soft tip section while their insulated conducting wires are passed through the shaft lumen to the proximal handle connector. The diameter of the tip electrode is generally larger than the shaft diameter.

In still another embodiment, a catheter probe system comprises a plurality of flexible longitudinally extending shafts each having a distal end, a proximal end, and a lumen extending therebetween, whereby an inflatable soft tip section substitutes the tip section in one or more of the catheter shafts of a basket type catheter system. Each individual shaft of the catheter system has a resilient soft tip section under an inflation pressure.

In one embodiment, a catheter of this invention has a separate inner lumen to be used for passage of conducting wires, and/or a guidewire for guiding the catheter into the blood vessel and the heart. The outer lumen having a wavy inflatable outer surface, comprising a plurality of hills and valleys, of this invention can be inflated to render electrodes-to-tissue intimate contacting during clinical procedures. In this embodiment, the inflation fluid can be injected from the fluid injection port into this co-centric outer luminal space to inflate the inflatable soft tip section. A double-lumen catheter shaft is used for this embodiment. The catheter system is consisted of two tubing sections: the distal soft inflatable tip section and the proximal main catheter shaft section. In order to provide increased torsional rigidity to the main catheter shaft, the main shaft material preferably comprises a polymeric tubing having a desired hardness. Preferably, the shaft will have a composite structure including a base layer of a relatively low Durometer material, a stiffening layer, for example, metal braid or coil, and an outer layer comprising the biocompatible polymeric material. To enhance biocompatibility, the catheter shaft, further comprises surface coating of heparin, hirudin, antibiotics, or the like on the blood or body tissue contacting surface of the catheter shaft.

A method for positioning a catheter having a soft inflatable tip section within a heart chamber comprises percutaneously introducing the distal end of a catheter through an aorta to the heart chamber, wherein electrodes are disposed at the distal section of the catheter; connecting the proximal handle to the catheter shaft; and inflate the distal end of the catheter about half an atmosphere or higher above the normal in vivo chamber pressure to enable the inflated tip section to curve or being assisted via a steerable mechanism to conform to the irregular intracardiac surface. Once at the desired location, the electrical signal obtained from the tissue to the electrodes on the inflated tip section can be transmitted to the exterior ECG monitor for cardiac mapping. Alternately, the radio frequency energy can be applied to one or more of the electrodes on the inflated tip section once an intimate contact with the tissue is achieved using the catheter of this invention.

The method and apparatus of the present invention have several significant advantages over known catheters. In particular, the intimate contact of electrodes against the desired intracardiac tissue by using a catheter having an inflatable soft tip section is achieved.

DETAILED DESCRIPTION OF EXEMPLARY EMBODIMENTS

Figure 1:
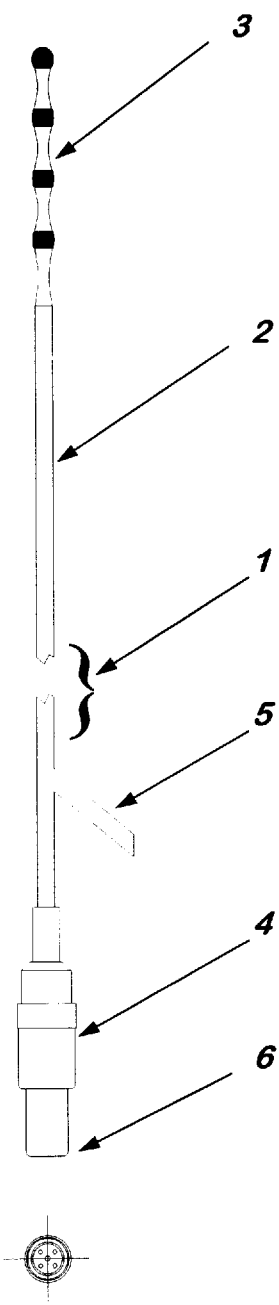
FIG. 1 is a front elevational view of the catheter with a set of electrodes and an inflatable tip section constructed in accordance with the principles of the present invention.

Referring to FIG. 1, a catheter system 1 constructed in accordance with the principles of the present invention comprises: a main catheter shaft section 2, an inflatable soft distal tip section 3, a proximal handle 4 and an inflation fluid infusion port 5. The handle 4 has a connector 6 for wires signal transmission to an EKG monitor or for radiofrequency energy transmitted from a radiofrequency generator. The distal tip section 3 is consisted of a tip electrode and multiple band electrodes on an inflatable tubing shaft.

Figure 2:
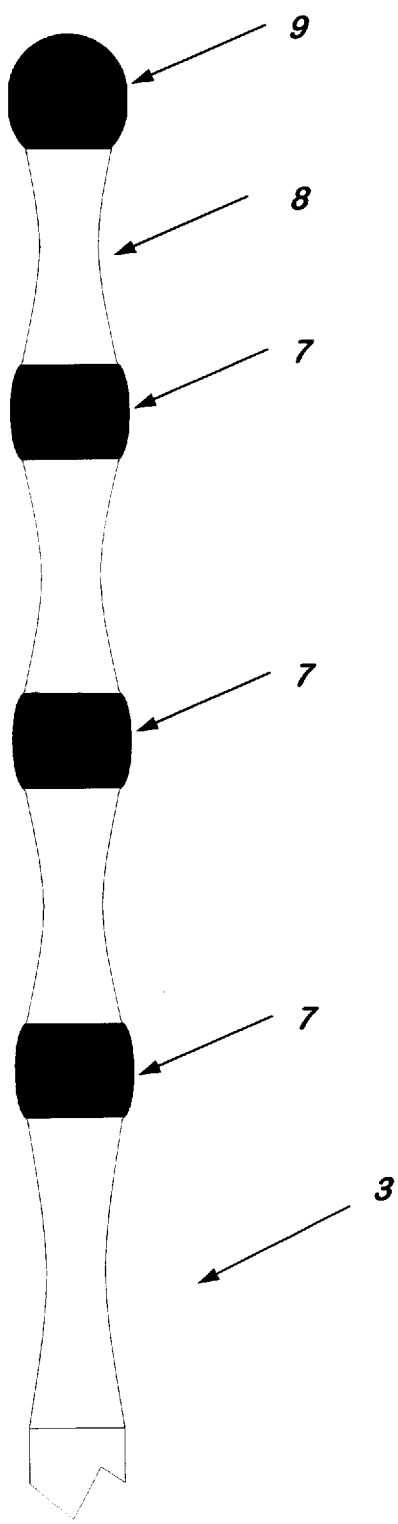
FIG. 2 is the inflatable tip section of the catheter of FIG. 1 under no inflation pressure.

FIG. 2 shows the inflatable soft tip section 3 of FIG. 1 under no inflation pressure, consisting of a tip electrode 9 and several band electrodes 7. The tip section is constructed of an inflatable tubing shaft 8. The band electrodes are located on and adhered to the "hills" of the wavy inflatable tubing shaft 8 of the tip section 3. The shape of the outer surface of the band electrodes is round. In one embodiment, the soft tip section may be reinforced internally by an inner lumen or tubing. The outer lumen or tubing is inflatable via an inflation pressure of the injected inflation fluid of this invention.

Figure 3:
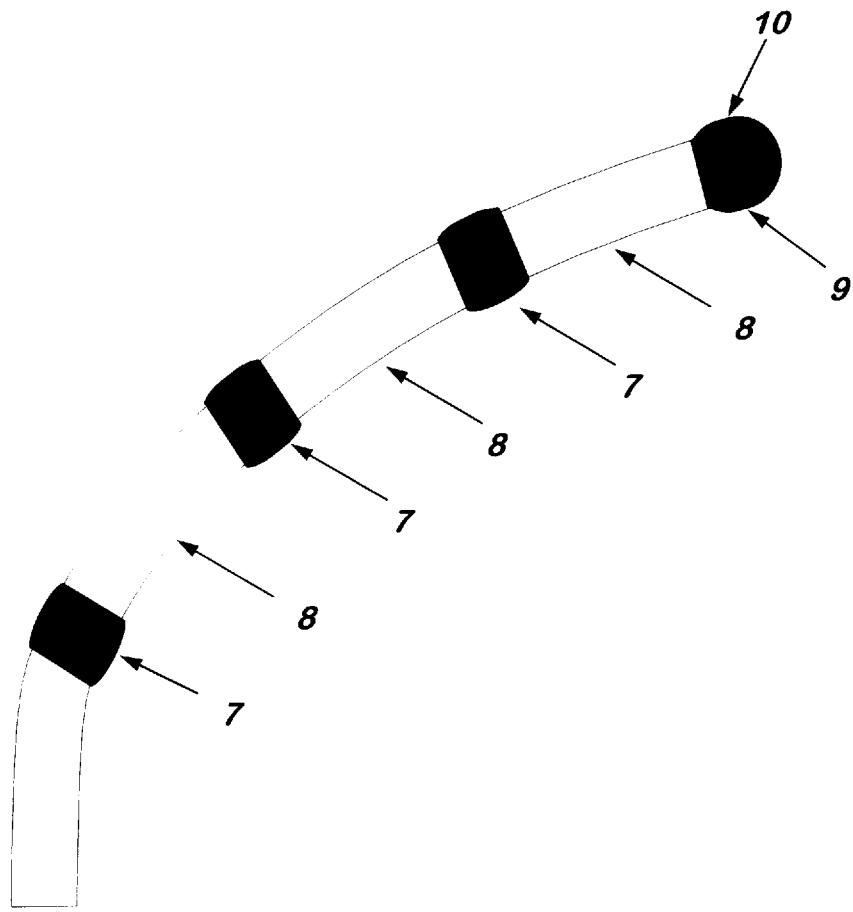
FIG. 3 is the inflatable tip section of the catheter under inflation pressure constructed in accordance with the principles of the present invention.

FIG. 3 shows the tip section under inflation pressure. The curvature of the tip section comes from the pre-shaping of the soft inflatable shaft or outer tubing. In another embodiment, the inflation fluid is injected into the outer side lumen in a double-lumen configuration in order to curve the tip section to conform to the pre-shaped pattern under an inflation pressure. In still another embodiment, the curvature can also come from a steerable mechanism at the proximal handle, if so desired. The purpose of the inflation pressure is to keep the tip section resilient and push the tip section outwardly against the tissue. The tissue contact point of the tip electrode is at point 10 when the catheter is pushed against the intracardiac surface. When higher inflation pressure is applied from the inflation infusion port 5 at the proximal end, the tip section 3 shall curve more and conform to the inner contour surface of the heart. By maintaining the electrodes surface round, the major contacting area between a catheter and the tissue is the electrode surfaces 7 and 9, rather than the tubing shaft surface 8.

Figure 4:
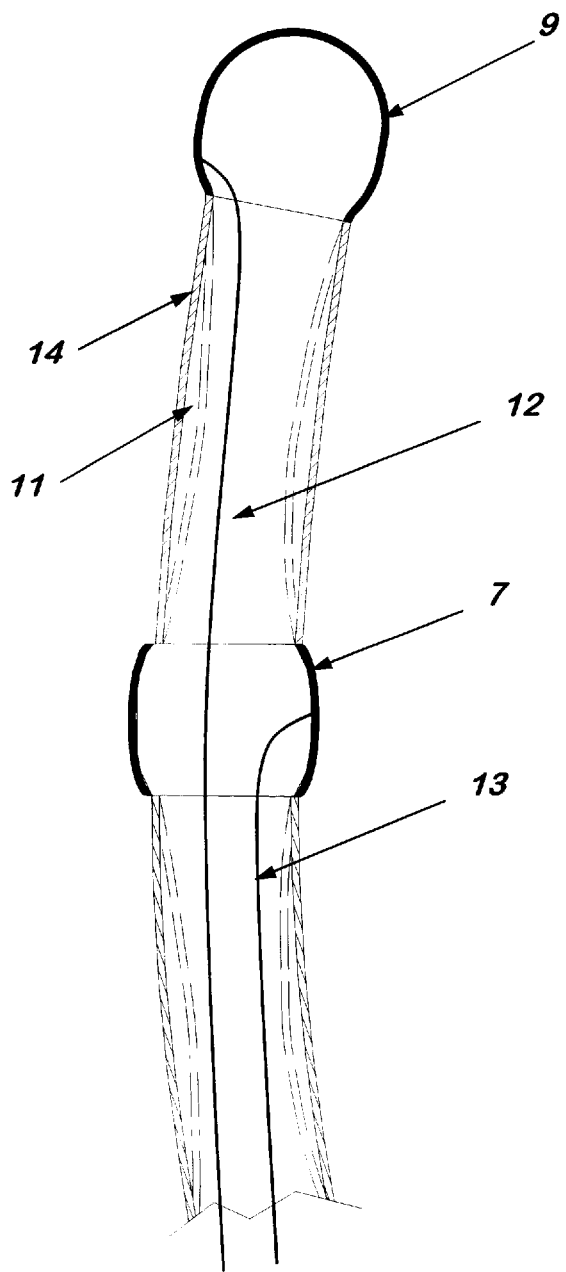
FIG. 4 is a close-up cross-sectional view of the tip section of the catheter under inflation pressure.

FIG. 4 is a close-up cross-sectional view of the tip section under inflation pressure. The dotted line 11 is the outer surface of the tubing shaft under no inflation pressure while the solid line 14 is the outer surface of the tubing shaft under an inflation pressure. The conducting wires 12 and 13 are used to transmit the electric signals from the electrodes 9 and 7 to the proximal connector 6. The conducting wires 12 and 13 are also used to transmit the radiofrequency energy to the electrodes for therapeutic ablation procedure.

The material of electrodes may include a noble metal or their alloy, such as platinum, iridium, silver or gold. The spacing between the electrodes is in the range of 1 mm to 10 mm, preferably 2 to 5 mm.

From the foregoing, it should now be appreciated that an improved catheter has been disclosed herein comprised of a set of multiple electrodes and an inflatable tip section to render a more intimate tissue contact. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter system comprising:

a catheter shaft having a distal portion, a distal end, a proximal end, and a least one lumen extending therebetween, wherein the distal portion of the catheter shaft is deflectable;

a handle attached to the proximal end of the catheter shaft, wherein the handle has a steering mechanism for deflecting the distal portion of said catheter shaft;

an inflatable wavy soft tip section at the distal portion of the catheter shaft, wherein the outer surface of said inflatable wavy soft tip section has a plurality of hills and valleys;

a plurality of conducting electrodes secured on the hills of said inflatable wavy soft tip section;

pressurization means for inflating the inflatable wavy soft tip section, wherein said inflatable wavy soft tip section is pre-shaped to form a generally straight configuration in an uninflated state and to form a curved configuration in an inflated state;

said conducting electrodes individually encircling said inflatable wavy soft tip section and having an outermost circumferential diameter larger than the outer diameter of the catheter shaft;

said valleys having an uninflated geometry wherein the uninflated diameter of the valleys is less than said outermost circumferential diameter of the conducting electrodes; and said valleys further having an inflated geometry wherein the inflated diameter of the vallevs is less than said outermost circumferential diameter of the conducting electrodes, but greater than the uninflated diameter of the valleys.

2. A catheter system of claim 1, wherein the steering mechanism comprises at least one core wire extending from the handle through the lumen of the catheter shaft and attaching to the distal end of the catheter shaft.

3. A catheter system of claim 1, wherein the material for the soft tip section is consisted of a non-compliant material.

4. A catheter system of claim 3, wherein the non-compliant material is selected from a group consisting of polyethylene, and polyethylene terephthalate.

5. A catheter system as in claim 1, further comprising a coating of heparin, hirudin, and antibiotics on the surface of the catheter shaft.

6. A catheter system as in claim 1, further comprising a coating of heparin, hirudin, and antibiotics on the surface of the conducting electrodes.

* * * * *